United States Patent
Aschmann et al.

(10) Patent No.: US 6,312,257 B1
(45) Date of Patent: Nov. 6, 2001

(54) BRUSH FOR USE IN RESTORATIVE DENTISTRY

(75) Inventors: Felix Aschmann, Arosio; Beat A. Von Weissenfluh, Gentilino, both of (CH)

(73) Assignee: Hawe Neos Dental Dr. H. V. Weissenfluh AG, Bioggio (CH)

( * ) Notice: Subject to any disclaimer, the term of this patent is extended or adjusted under 35 U.S.C. 154(b) by 0 days.

(21) Appl. No.: 09/658,943

(22) Filed: Sep. 11, 2000

(30) Foreign Application Priority Data

Sep. 20, 1999 (CH) .................................................. 1726/99

(51) Int. Cl.[7] .......................................................... A61C 3/02
(52) U.S. Cl. .......................... 433/165; 433/125; 15/167.1
(58) Field of Search .................................. 433/165, 166, 433/142, 125; 15/106, 167.1

(56) References Cited

U.S. PATENT DOCUMENTS

| | | |
|---|---|---|
| 2,311,135 | 2/1943 | Steinmetz et al. . |
| 2,750,614 * | 6/1956 | Collins et al. ........................ 401/132 |
| 2,842,844 * | 7/1958 | Seal ........................................ 433/166 |
| 2,984,053 | 5/1961 | Peterson . |
| 3,609,789 * | 10/1971 | Slater .................................. 15/104.94 |
| 4,624,876 * | 11/1986 | Nevin ...................................... 428/65 |
| 4,739,532 * | 4/1988 | Behrend .................................... 15/28 |
| 5,187,904 | 2/1993 | Tyler et al. ............................. 51/330 |
| 5,588,172 | 12/1996 | Biocca ................................... 15/179 |

FOREIGN PATENT DOCUMENTS 2439066  5/1998  (FR) .

* cited by examiner

Primary Examiner—John J. Wilson
Assistant Examiner—Melba Bumgarner
(74) Attorney, Agent, or Firm—Young & Thompson

(57) ABSTRACT

Instead of a bunch of bristles coated with abrasive particles, the brush for surface treatments in restorative dentistry comprises one or several lamellar abrasive elements. In the manner of a lametta strip, the abrasive elements are divided by at least one incision, such that a plurality of bristle portions is obtained. Due to the planar configuration of the bristle portions themselves, the latter are easily bendable in at least one direction. If the arrangement of the abrasive elements is such that this direction of easy bending ability is approximately tangential to the intended rotational direction of the brush, the overall flexibility of the brush is substantially increased, thus allowing a substantially improved compliance with application-specific requirements.

15 Claims, 2 Drawing Sheets

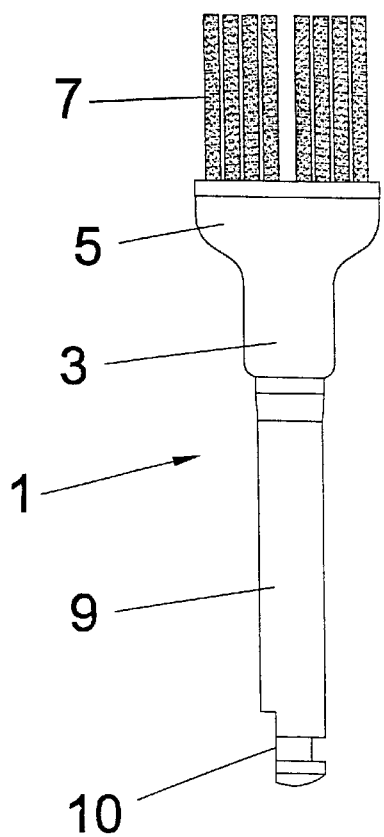
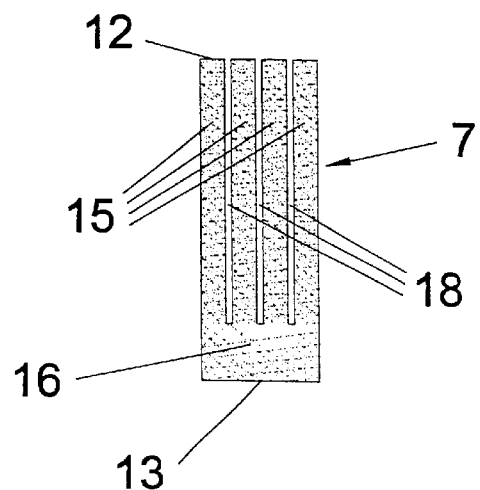
Fig. 1
Fig. 2
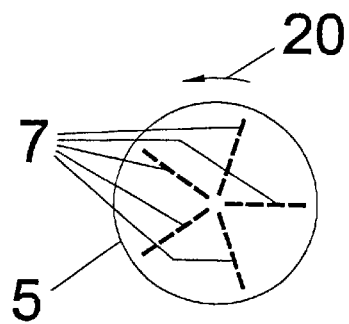
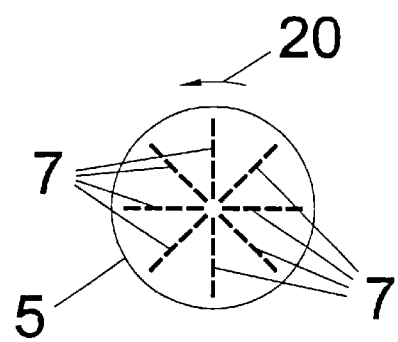
Fig. 3
Fig. 4

BRUSH FOR USE IN RESTORATIVE DENTISTRY

FIELD OF THE INVENTION

The present invention relates to a brush used in restorative dentistry for the treatment of surfaces, more particularly of fillings.

BACKGROUND OF THE INVENTION

In restorative dentistry, it is usual after the application of a filling to produce the desired shape and surface structure thereof in several steps, starting from the coarse working of the anatomic shape by means of diamond cutters up to the polishing of the filling surface. This process involves many instrument changes as instruments of different grain are required between the coarse shaping and the polishing operation.

Another problem is the fact that the surfaces of teeth have complex shapes and the usual polishing instruments only poorly adapt to the fissured surfaces, so that the instruments must be carefully guided in order to reach all portions that have to be polished.

An important improvement in this respect has been attained by the use of brushes whose bristles are coated with abrasive particles. These brushes allow one to polish the filling in a single step directly after the coarse shaping by means of diamond cutters. Furthermore, highly edged and angular structures can be reached without a special guidance of the instrument.

However, these brushes exhibit a number of serious drawbacks which are mainly due to the fact that the bristles, on account of the abrasive particles, are relatively thick:

1. They are stiff and unwieldy;
2. they have the character of a technical brush and seem inconvenient for oral applications;
3. they are very traumatic to the gums (stiffness);
4. they adapt to the tooth surface only if considerable pressure is applied;
5. due to the thick bristles, not all shapes can be manufactured;
6. the thick bristles are hardly elastic and will break under high stress;
7. they are problematic with respect to hygiene: they are too expensive for one-way use, yet they can only be sterilized but not cleaned.

In the production of dental replacements such as crowns, inlays, bridges, etc., i.e. in the field of the dental technician, similar requirements are encountered. Consequently, the above considerations also apply to grinding tools intended for this area.

SUMMARY OF THE INVENTION

It is therefore an object of the present invention to provide a brush for use in dentistry, more particularly in restorative dentistry, which represents an improvement with respect to at least one of the above-mentioned problems.

This object is attained by a brush comprising at least one essentially lamellar abrasive element attached to the head of a holder and having at least one incision in order to divide the abrasive element into at least two bristle portions which are bendable essentially independently from each other. Preferred embodiments of the invention are defined in the dependent claims.

In other terms, the solution according to the invention consists in finding a way of producing more flexible but still abrasive bristles. According to the invention, these are obtained when sheets coated with abrasive materials are provided with incisions of a certain depth at suitable intervals, thereby producing a number of lamellar strips which are connected to each other at one end.

BRIEF DESCRIPTION OF THE DRAWINGS

The invention will be further explained hereinafter with reference to an exemplary embodiment illustrated in the figures.

FIG. 1 shows a lateral view of a brush of the invention;

FIG. 2 shows an abrasive strip in an enlarged view;

FIGS. 3 and 4 show top views of two alternative embodiments of the brush; and

DETAILED DESCRIPTION OF THE INVENTION

Figure 5:
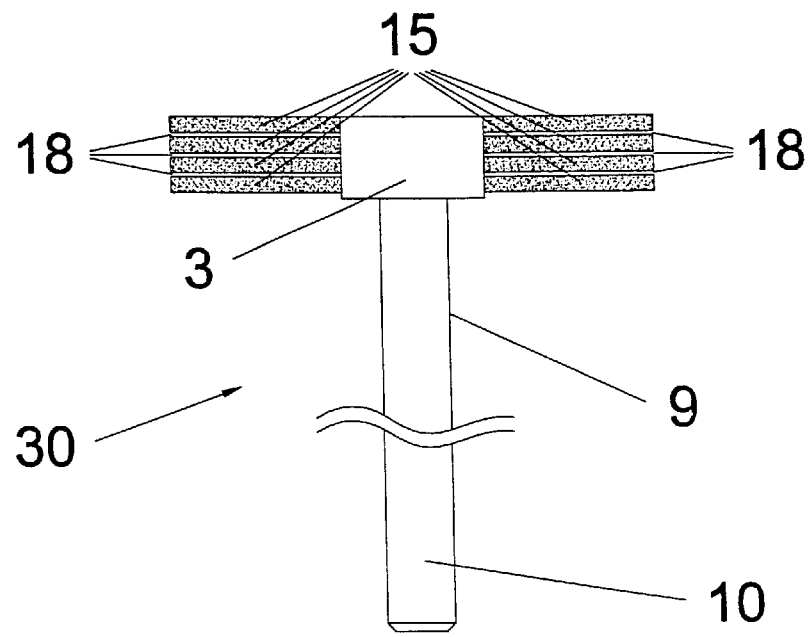
FIGS. 5 and 6 schematically show a second embodiment in a longitudinal section and in a top view, respectively.

Brush 1 is essentially composed of a holder 3 on the head 5 on which abrasive strips 7 are attached. Otherwise, holder 3 corresponds to commercially available brushes: beside head 5, it includes a shaft 9 whose distal end comprises an adapter 10 for its connection to a conventional drive for dental technical work.

In FIG. 2, abrasive strip 7 is illustrated on a larger scale. It is composed of a support in the form of a foil which is coated with abrasive particles symbolized by dots. The support may be made from various materials such as metal, synthetic materials, or paper. The abrasive coating may be one- or two-sided. Abrasive strip 7 is divided into regular sections by incisions extending from one of its narrow sides 12 almost up to the second narrow side 13, resulting in lamellar bristles 15 which are connected to each other at end 16, i.e. on narrow side 13. In this respect, abrasive strip 7 resembles a lametta strip. The number of incisions 18 may vary within large limits. There may be 1 to 20 incisions, for example, or a greater number. Incisions 18 do not necessarily have to be arranged at regular intervals, even though an arrangement at constant intervals is most obvious.

The brush is formed by a number of abrasive strips 7 which are uprightly attached to head 5. For example, connecting end 16 may be clamped in head 5, or in the case of a head of synthetic material, it may be fastened by injection-molding.

FIGS. 3 and 4 show two different, exemplary arrangements of 5 and 8 abrasive strips in head 5.

In the figures, arrow 20 indicates the rotational direction for which the tool is intended. Preferably, the abrasive strips will be arranged approximately transversely to the direction of motion. Due to the essentially radial disposition of the abrasive strips, the bristles have a relatively high stiffness in the direction of the centrifugal force, so that an outward bending is suppressed and the brush conserves its defined contour even at high rotational speeds.

Figure 6:
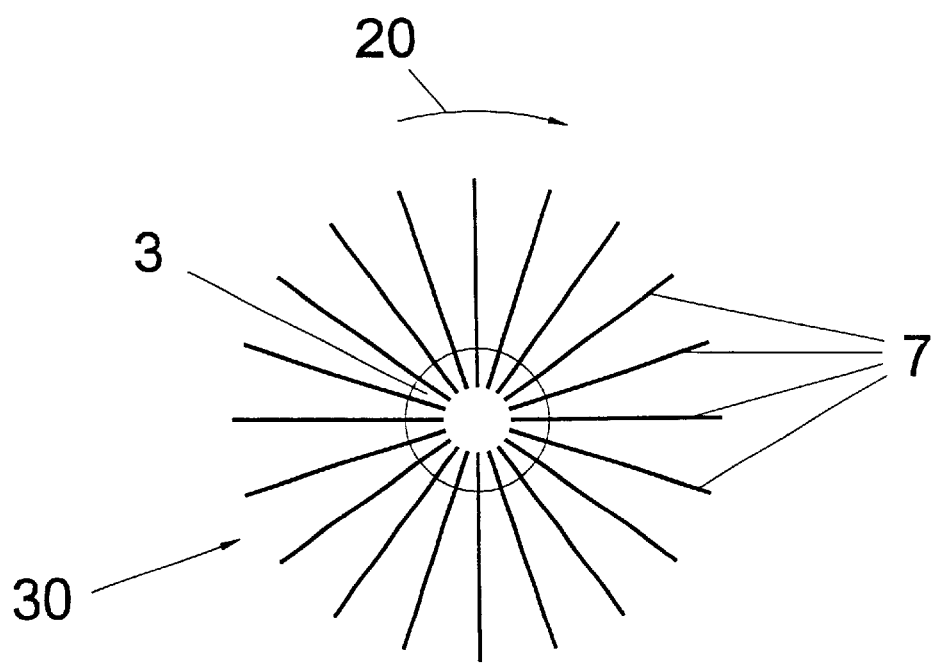

In this form, the described embodiment is suitable both for dentists for the treatment of fillings and for dental technicians. A second embodiment which is particularly intended for the latter is shown in FIGS. 5 and 6.

The abrasive strips 7 of this brush 30 are so arranged that incisions 18 and thus the lamellar bristles 15 are directed radially outwards. The other characteristic features correspond to those described above and are designated by the same reference numerals.

Due to the realization of the bristles in the form of thin strips whose ability to be bent in the direction tangentially to the rotation of the brush is clearly superior to that of conventional bristles having e.g. an approximately round cross-section, a slight pressure is already sufficient for the brush to adapt even to complicated structures. Abrasive strips 7 are inexpensive in manufacture and can be provided with almost any contour e.g. by cutting them to shape.

A great number of modifications of the brush of the invention are apparent to those skilled in the art without leaving the scope of the invention. Thus it is e.g. possible not to arrange the abrasive strips exactly, but only approximately radially. One such arrangement would be that of a cross where each arm is composed of two or more parallel abrasive strips. Also, a wave-shaped form is possible instead of the illustrated flat form of the abrasive strips. Besides the usual rotative working movement, a linear movement is also conceivable, e.g. a reciprocating one. Any abrasive material may be considered which is appropriate for coating suitable lamellar supports and otherwise meets the requirements of dental technique.

What is claimed is:

1. A dental tool, comprising:
   a bristle sheet having a support material coated with an abrasive material, the bristle sheet having incisions partitioning the sheet into plural, adjacent lamellar strips connected to each other at one end to provide plural strips in a width direction of the bristle sheet and only one strip thick in a thickness direction of the bristle sheet;
   a rotatable tool head supporting the bristle sheet; and
   a shaft at a first end supporting the tool head and at a second end including a drive adapter.

2. The tool of claim 1, wherein the abrasive material comprises abrasive particles and the support material is metal.

3. The tool of claim 1, wherein,
   the bristle sheet has a thickness, a length, and a width, the thickness being the smallest dimension,
   the bristle sheet having two planar surfaces defined by the length and the width, both of the two planar surfaces being coating by the abrasive material,
   the abrasive material comprising abrasive particles, and
   the bristle sheet being flexible along the length of the bristle sheet.

4. The tool of claim 1, comprising a plurality of the bristle sheets mounted on the head by injection-molding, and
   wherein the lamellar strips are substantially parallel to a length of the shaft.

5. The tool of claim 1, comprising a plurality of the bristle sheets mounted, and
   wherein the lamellar strips are substantially perpendicular to a length of the shaft and bend in a direction substantially tangentially to an intended direction of rotation of the head.

6. The tool of claim 1, wherein the lamellar strips are flexible in only a single direction and adapt to complicated structures under a slight pressure.

7. The tool of claim 1, wherein the abrasive material comprises abrasive particles and the support material is a synthetic material or a paper material.

8. A dental polishing brush, comprising:
   a rotatable brush head with a mounting surface;
   a brush shaft at a first end supporting the brush head and at a second end having a drive adapter; and
   plural bristle sheets attached to the mounting surface of the brush head,
   each of the bristle sheets being made of a support material coated with an abrasive material,
   each bristle sheet having incisions partitioning the sheet into plural, adjacent lamellar strips
   connected at connecting end to provide plural strips in a width direction of each bristle sheet and only one strip in a thickness direction of the bristle sheet.

9. The brush of claim 8, wherein the abrasive material comprises abrasive particles and the support material is metal.

10. The brush of claim 8, wherein,
    the bristle sheets have a thickness, a length, and a width, the thickness being the smallest dimension,
    the bristle sheets having two planar surfaces defined by the length and the width, both of the two planar surfaces being coating by the abrasive material,
    the abrasive material comprising abrasive particles, and
    the bristle sheet being flexible along the length of the bristle sheet.

11. The brush of claim 10, wherein, the abrasive material is limited to the two planar surfaces and all edges of the bristle sheets are free of the abrasive material.

12. The brush of claim 8, wherein, the bristle sheets are mounted substantially parallel to a length of the shaft.

13. The brush of claim 8, wherein, the lamellar strips are substantially perpendicular to a length of the shaft and bend in a direction substantially tangentially to a direction of rotation of the head.

14. The brush of claim 8, wherein the lamellar strips are flexible in only a single direction and adapt to complicated structures under a slight pressure.

15. The brush of claim 8, wherein the abrasive material comprises abrasive particles and the support material is a synthetic material or a paper material.

* * * * *